United States Patent [19]

Shepard et al.

[11] 3,956,374

[45] May 11, 1976

[54] ARYL-OXO-HEPTENOIC ACIDS

[75] Inventors: Kenneth L. Shepard, Ambler; Edward J. Cragoe, Jr., Lansdale; Wasyl Halczenko, Hatfield, all of Pa.

[73] Assignee: Merck & Co., Inc., Rahway, N.J.

[22] Filed: May 3, 1974

[21] Appl. No.: 466,667

[52] U.S. Cl. .............................. 260/515 A; 260/269; 260/298; 260/313.1; 260/429.9; 260/439 R; 260/473 R; 260/469; 260/515 R; 260/526 N; 260/558 R; 260/559 R; 424/287; 424/289; 424/295; 424/308; 424/317; 424/324
[51] Int. Cl.² ........................................ C07C 63/00
[58] Field of Search ........ 260/240 R, 240 K, 515 R, 260/515 A, 520, 520 A, 520 B, 520 C

[56] References Cited
UNITED STATES PATENTS 3,042,714   7/1962   Schultz et al. ..................... 260/520

OTHER PUBLICATIONS

Krauch et al., Organic Name Reactions, John Wiley & Sons, N.Y., N.Y., 1964 p. 96.

*Primary Examiner*—Arthur P. Demers
*Attorney, Agent, or Firm*—Hesna J. Pfeiffer; Thomas E. Arther; Harry E. Westlake, Jr.

[57]   ABSTRACT

Novel 4-phenyl-4-substituted-5-oxo-7-aryl-heptanoic acids are prefaced by either of two synthetic processes. The first method involves the reaction of a 4-phenyl-4-substituted-5-oxo-hexanoic acid with an arylcarboxyaldehyde. The second method involves reaction of an arylcarboxaldehyde with an appropriate ketone, treatment of the product with an acrylic acid ester, followed by hydrolysis of the resulting ester. The compounds of the invention are prostaglandin antagonists and are particularly useful as topical antiinflammatory agents.

8 Claims, No Drawings

ARYL-OXO-HEPTENOIC ACIDS

SUMMARY OF THE INVENTION

This invention relates to a new class of aryl-oxo-heptenoic acids. More particularly, these compounds can be described as a group of 4-phenyl-5-oxo-6-heptenoic acids having a 4-aralkyl(or 4-aralkenyl) and a 7-aryl substituent. The salts, esters and amides of such carboxylic acids are also included within the ambit of the invention. There are also provided by this invention synthetic processes for making these compounds. Additional objects and purposes of the invention will become clear from the ensuing detailed description of it.

The new 4-phenyl-oxo-heptenoic acids of this invention may be generally represented by the formula:

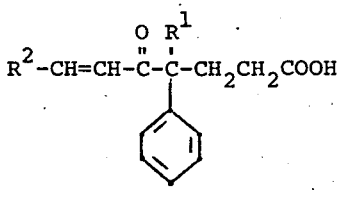

(I)

$R^1$ in Formula I is aralkyl or aralkenyl, preferably benzyl or cinnamyl. The aromatic ring of either of these groups can be nuclearly substituted with 1 or 2 substituents, such as halo, e.g., chloro, bromo, iodo, or fluoro; lower-alkyl or loweralkoxy both of 1–4 carbon atoms, such as methyl, ethyl, propyl, butyl, methoxy, ethoxy, isopropoxy, and the like. Particularly preferred substituents are chloro, bromo, methyl, or methoxy.

$R^2$ in Formula I is phenyl, optionally substituted with 1 or 2 nuclear substituents, which can be halo, e.g., chloro, bromo, iodo, or fluoro; loweralkyl or loweralkoxy both of 1–4 carbon atoms, such as methyl, ethyl, propyl, butyl, methoxy, ethoxy, isopropoxy, and the like. Particularly preferred substituents are chloro, bromo, methyl, or methoxy.

When either $R^1$ or $R^2$ is substituted, the substituents can be the same or different independently on each of $R^1$ or $R^2$.

Preferably, $R^1$ is benzyl or cinnamyl optionally having 1–2 substituents, such as chloro, bromo, methyl, methoxy, or dichloro; and $R^2$ is phenyl having at least 1 substituent which is chloro, methyl, methoxy, or di-substitution which is dichloro.

Formula I represents a free carboxylic acid, and such free acids are frequently referred to in the description of this invention. It is to be understood, however, that also included within the scope of this invention are the salts, esters and amides of the free acids. Included and preferred within the salts are the pharmacologically acceptable salts such as those formed with pharmacologically acceptable metal cations, ammonium, amine and quaternary ammonium cations. Examples include the alkali and alkaline earth metal salts, e.g., sodium, potassium, lithium, mangesium, calcium. Cations of heavy metals such as iron, zinc and manganese may also be used. Amine salts may be obtained from primary, secondary or tertiary amines, examples being methylamine, dimethylamine, triethylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and loweralkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing hydrophilic groups, e.g., mono, di-, and triethanolamine, ethyldiethanolamine, N-butylethanolamine, 2-amino-1-butanol, and 2-amino-2-ethyl-1,3-propanediol.

As esters, there are included the loweralkyl, aryl, aralkyl, aralkenyl and acyloxyalkyl esters, examples of which are methyl, ethyl, propyl, isopropyl, t-butyl, hexyl, phenyl, benzyl, cinnamyl, acetoxymethyl, pivaloyloxymethyl, benzhydryl, methoxymethyl esters.

DISCUSSION OF THE PRIOR ART

U.S. Pat. No. 3,042,714 relates to 4-aryl-4-arylkyl-5-oxohexanoic acid derivatives. These compounds are particularly useful as bactericidal, bacteriostatic, virucidal, and virustatic agents.

The Journal of Organic Chemistry, Vol. 22, page 1338, (1957), discloses the compounds patented above, and J. Org. Chem., 23, 971 (1958) discloses lower homologues of the patented compounds.

All of these compounds in the literature differ in a number of critical aspects from those claimed herein. The latter are of a longer alkyl chain, have unsaturation in the claim, have a terminal aryl substituent adjacent to the unsaturation, and moreover have markedly different utilities. The compounds of the art are primarily antiviral agents, while the compounds claimed herein are topical anti-inflammatory agents.

MODE OF ADMINISTRATION

When the compounds of this invention are used as topical anti-inflammatory agents, they can be formulated into a lotion, ointment, aerosol, or cream in combination with the usual pharmaceutically acceptable diluents.

Generally speaking, the compositions are prepared containing from about 0.05 to about 5% by weight of the substituted heptenoic acids.

For example, a hydrophilic ointment can be prepared containing 4-(o-chlorobenzyl)-4-phenyl-5-oxo-7-(p-chlorophenyl)-6-heptenoic acid (0.5% by weight), dipropylene glycol and polyethylene glycol by adding the acid as an amine salt to a warm solution of dipropylene glycol in polyethylene glycol ("Carbowax", molecular weight 1000). On agitation a cloudy suspension results. Cooling to room temperature gives an ointment of good consistency. Ointments can be prepared having a 0.05 to 1% by weight of the desired compound.

A cream-type preparation can also be prepared as a carrier for the active ingredient. A polyethylene glycol (MW of 200–300) containing 0.75% of 4-(2,4-dichlorobenzyl)-4-phenyl-5-oxo-7-(p-chlorophenyl)-6-heptenoic acid is mixed together with benzyl alcohol, benzyl benzoate, and sodium stearate. A translucent viscous cream results. Creams of this nature can be prepared having 0.05–1% by weight of the desired compound.

The active compounds of this invention can also be mixed into pharmaceutical compositions as solid ointment sticks (the desired compound is dissolved in a non-volatile, non-toxic viscous organic solvent, such as isopropylene glycol, and then a hardening agent such as polyglyceride, a polyethylene glycol or acetyl alcohol is added; once the mixture is homogenous, it can be molded into the desired shape) or lotions. The latter can be oil-in-water or water-in-oil base type suspensions, using waxes and esters which are non-toxic and generally used in the art.

In addition, these compounds can be administered using methods involving an aerosol liquid or micronized powder spray.

The topical compositions are applied to the skin daily or twice or three times a day. The dosage can be obtained indefinitely.

PROCESS OF THE INVENTION

The compounds of this invention can be prepared by either of two synthetic methods. The first involves the reaction of a 4-phenyl-4-substituted-5-oxo-hexanoic acid with an arylcarboxaldehyde ($R^2$CHO) in the presence of a strong base, such as alkali metal hydride, amide, alkoxide, or hydroxide, e.g., sodium hydroxide, sodium hydride, sodium amide, sodium ethoxide, potassium tert-butoxide or potassium hydroxide. This reaction is conducted in an inert solvent or solvent system, such as water, ethanol, dimethylformamide, etc., at a temperature ranging from 40°–120°C. The reactants are employed in approximately equimolar amounts. The reaction can be schematically depicted as follows:

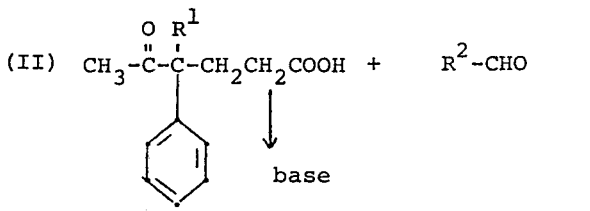

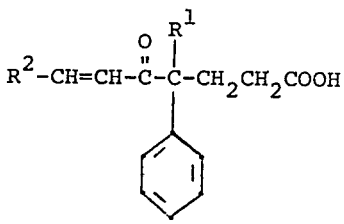

The starting reactant, the 4-phenyl-4-substituted-5-oxohexanoic acid, is prepared following procedures available in the art, e.g., U.S. Pat. No. 3,042,714, or by methods taught in more detail hereinafter.

The second synthetic method for preparing compounds of this invention involves first reacting an arylcarboxaldehyde ($R^2$CHO) with a substituted acetone, e.g.,

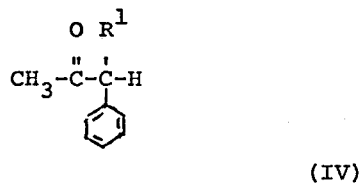

to prepare as unsaturated ketone, e.g.,

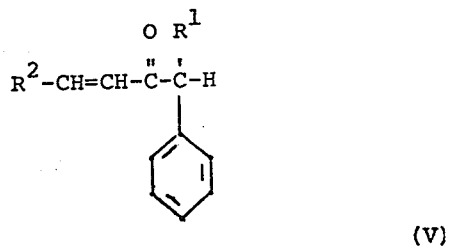

This latter reaction takes place in the presence of a strong base, as defined above, in an inert solvent such as water or ethanol, at a temperature of 25°–120°C., in from about 4–36 hours.

The product V is then reacted with a loweralkyl (1–4 carbon atoms) acrylate, such as methyl acrylate or ethyl acrylate.

This reaction takes place in an inert solvent, such as glyme or diglyme. The loweralkyl ester group is then removed from the resulting ester of I by mild base hydrolysis and the desired product I recovered upon acidification of the reaction mixture.

It will be apparent that optically active isomers of any of the compounds of Formula I can be prepared by using optically active starting compounds or reactants, or by optical resolution following synthesis.

The free acid of Compound I can be derivatized in a variety of ways to yield the various salts, esters, and amides of the acid. To obtain carboxy salts, the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine, or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxylic acid esters, the acid products are treated in ether with an ethereal solution of the appropriate diazoalkane. For example, methyl esters are produced by reaction of the acid products with diazomethane. To obtain products wherein the acid derivative is carbamoyl, substituted carbamoyl, or carbazoyl, the acid product is first converted to an active woodward ester. For example, the carboxylic acid product can be made to react with N-tert butyl-5-methylisoxazolium perchlorate in acetonitrile in the presence of a base such as triethylamine to yield an active ester, i.e., where —COOH is converted to

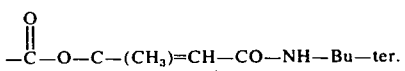

Active esters of this type can be reacted with ammonia to yield carbamoyl derivatives or with primary or secondary carbamoyl derivatives, and with hydrazine to yield carbazoyl derivatives.

This invention is further illustrated by the following examples.

EXAMPLE 1

4-(2,4-Dichlorobenzyl)-4-phenyl-5-oxo-7-(p-chlorophenyl)-6-heptenoic Acid p-Chlorobenzaldehyde (3.5 g., 0.025 mole) in ethanol (10 ml.) is added to a solution of 4-(2,4-dichlorobenzyl)-4-phenyl-5-oxohexanoic acid (5.48 g., 0.015 mole) and sodium hydroxide (0.80 g., 0.03 mole) in water (50 ml.). The resulting mixture is heated on a steam bath for 24 hours. Then the reaction solution is cooled to room temperature, diluted with water (200 ml.) and extracted with ether to remove the excess p-chlorobenzaldehyde. The aqueous phase is then acidified with dilute hydrochloric acid (10 ml.), and the sticky solid which precipitates is filtered and air-dried, yield 5.5 g., m.p. 215°–226°C. Recrystallizations from ethanol gives material with m.p. 224.5°–227°C.

Anal. Calcd. for $C_{26}H_{21}Cl_3O_3$: C, 64.01; H, 4.34; Found: C, 63.87; H, 4.28.

EXAMPLE 2

4-(3,4-Dichlorobenzyl)-4-phenyl-5-oxo-7-(p-chlorophenyl)-6-heptenoic Acid p-Chlorobenzaldehyde (3.5 g., 0.025 mole) in ethanol (10 ml.) is added to a solution of 4-(3,4-dichlorobenzyl)-4-phenyl-5-oxohexanoic acid (5.48 g., 0.015 mole) and sodium hydroxide (0.80 g., 0.02 mole) in water (50 ml.). The resulting mixture is heated on a steam bath for 24 hours. Then the reaction solution is cooled to room temperature, diluted with water (250 ml.), and extracted with ether to remove the excess p-chlorobenzaldehyde. The aqueous phase is then acidified with dilute hydrochloric acid (15 ml.). The organic material which separates is extracted into ether, washed with saturated brine, and dried over $Na_2SO_4$. The ether is removed in vacuo, and trituration of the residue with ethanol (25 ml.) produces 1.6 g. of solid. Recrystallization from butyl chloride gives material with m.p. 155°–156.5°C.

Anal. Calcd. for $C_{26}H_{21}Cl_3O_3$: C, 64.01; H, 4.34; Found: C, 63.97; H, 4.34.

EXAMPLE 3

4-(o-Chlorobenzyl)-4-phenyl-5-oxo-7-(p-chlorophenyl)-6-heptenoic Acid p-Chlorobenzaldehyde (3.5 g., 0.025 mole) in ethanol (10 ml.) is added to a solution of 4-(o-chlorobenzyl)-4-phenyl-5-oxohexanoic acid (4.89 g., 0.015 mole) and sodium hydroxide (0.80 g., 0.03 mole) in water (50 ml.). The resulting mixture is heated on a steam bath for 24 hours. The reaction solution is cooled to room temperature, acidified with dilute hydrochloric acid (10 ml.), and the sticky solid which forms after scratching is filtered and air-dried, yield 7.0 g., m.p. 190°–213°C. Several recrystallizations from nitromethane, followed by a final recrystallization from acetonitrile, gives a light yellow solid with m.p. 223°–227°C.

Anal. Calcd. for $C_{26}H_{22}Cl_2O_3$: C, 68.88; H, 4.89; Found: C, 69.08; H, 4.71.

EXAMPLE 4

Dextro-4-(o-chlorobenzyl)-4-phenyl-5-oxo-7-(p-chlorophenyl)-6-heptenoic Acid p-Chlorobenzaldehyde (3.5 g., 0.025 mole) in ethanol (10 ml.) is added to a solution of dextro-4-(o-chlorobenzyl)-4-phenyl-5-oxohexanoic acid (4.89 g., 0.015 mole) and sodium hydroxide (0.80 g., 0.02 mole) in water (50 ml.). The resulting mixture is heated on a steam bath for 24 hours. The reaction solution is cooled to room temperature, acidified with dilute hydrochloric acid (10 ml.), and the yellow solid which precipitates is collected and air-dried, yield 7.1 g., m.p. 125°–157°C. Several recrystallizations from n-butyl chloride yields a white solid with m.p. 184.5°–187°C.

Anal. Calcd. for $C_{26}H_{22}Cl_2O_3$: C, 68.88; H, 4.89; Found: C, 69.03; H, 4.84.

EXAMPLE 5

Levo-4-(o-chlorobenzyl)-4-phenyl-5-oxo-7-(p-methoxyphenyl)-6-heptenoic Acid p-Methoxybenzaldehyde (3.4 g., 0.025 mole) in ethanol (10 ml.) is added to a solution of levo-4-(o-chlorobenzyl)-4-phenyl-5-oxohexanoic acid (4.89 g., 0.015 mole) and sodium hydroxide (0.80 g., 0.02 mole) in water (50 ml.). The resulting mixture is heated on a steam, bath for 24 hours. The reaction solution is cooled to room temperature, acidified with dilute hydrochloric acid (10 ml.), and the sticky solid which forms after scratching is filtered and air-dried. Recrystallization from n-butyl chloride yields 3.2 g., m.p. 152°–157°C. An additional recrystallization from n-butyl chloride yields material with m.p. 159°–160.5°C.

Anal. Calcd. for $C_{27}H_{25}ClO_4$: C, 72.24; H, 5.61; Found: C, 72.36; H, 5.55.

EXAMPLE 6

Levo-4-(o-chlorobenzyl)-4-phenyl-5-oxo-7-(p-methylphenyl)-6-heptenoic Acid p-Methylbenzaldehyde (3.00 g., 0.025 mole) in ethanol (10 ml.) is added to a solution of levo-4-(o-chlorobenzyl)-4-phenyl-5-oxohexanoic acid (4.89 g., 0.015 mole) and sodium hydroxide (0.80 g., 0.20 mole) in water (50 ml.). The resulting mixture is heated on a steam bath for 24 hours. The reaction solution is cooled to room temperature, acidified with dilute hydrochloric acid (10 ml.), and the sticky solid which forms after scratching is collected and air-dried, yield 7.4 g., m.p. 120°–147°C. Recrystallization from methylcyclohexane, followed by recrystallization from n-butyl chloride, yields a white solid with m.p. 166°–168.5°C.

Anal. Calcd. for $C_{27}H_{25}ClO_3$: C, 74.90; H, 5.82; Found: C, 75.01; H, 5.72.

EXAMPLE 7

4-(o-Bromobenzyl)-4-phenyl-5-oxo-7-(p-chlorophenyl)-6-heptenoic Acid p-Chlorobenzaldehyde (2.81 g., 0.02 mole) in ethanol (10 ml.) is added to a solution of 4-(o-bromobenzyl)-4-phenyl-5-oxohexanoic acid (3.0 g., 0.006 mole) and sodium hydroxide (0.56 g., 0.014 mole) in water (50 ml.). The resulting mixture is heated on a steam bath for 24 hours. The reaction solution is cooled to room temperature, diluted with water (200 ml.), and extracted with ether to remove the excess p-chlorobenzaldehyde. Ether is expelled from the aqueous phase by warming. The solution is cooled, acidified with dilute hydrochloric acid (10 ml.), and the yellowish solid which precipitates is collected and air-dried to yield 3.5 g. Recrystallization from ethanol gives material with m.p. 210°–213.5°C.

Anal. Calcd. for $C_{26}H_{22}BrClO_3$: C, 62.73; H, 4.46; Found: C, 62.45; H, 4.64;

EXAMPLE 8

Levo-4-(o-Chlorobenzyl)-4-phenyl-5-oxo-7-(m-chlorophenyl)-6-heptenoic Acid m-Chlorobenzaldehyde (3.5 g., 0.025 mole) in ethanol (10 ml.) is added to a solution of levo-4-(o-chlorobenzyl)-4-phenyl-5-oxohexanoic acid (4.89 g., 0.015 mole) and sodium hydroxide (0.8 g., 0.02 mole) in water (50 ml.). The resulting mixture is heated on a steam bath for 24 hours. The reaction solution is cooled to room temperature, diluted with water (300 ml.), and extracted with ether to remove the excess m-chlorobenzaldehyde. Ether is expelled from the aqueous phase by warming. The solution is cooled in an ice bath, acidified with dilute hydrochloric acid (10 ml.), and the off-white solid that precipitates is filtered and air-dried. Several recrystallizations from n-butyl chloride yields 3.15 g. of material with m.p. 170°–172°C.

Anal. Calcd. for $C_{26}H_{22}Cl_2O_3$: C, 68.88; H, 4.89; Found: C, 68.50; H, 4.99.

EXAMPLE 9

4-(p-Chlorobenzyl)-4-phenyl-5-oxo-7-(p-chlorophenyl)-6-heptenoic Acid p-Chlorobenzaldehyde (2.81 g., 0.02 mole) in ethanol (10 ml.) is added to a solution of 4-(p-chlorobenzyl)-4-phenyl-5-oxohexanoic acid (3.0 g., .009 mole) and sodium hydroxide (0.56 g., 0.014 mole) in water (50 ml.). The resulting mixture is heated on a steam bath for 24 hours. The reaction solution is cooled to room temperature, diluted with water (200 ml.), and extracted with ether to remove the excess p-chlorobenzaldehyde. Ether is expelled from the aqueous phase by warming. The solution is cooled in an ice bath, acidified with dilute hydrochloric acid (10 ml.), and the yellowish solid which precipitates is collected and air-dried to yield 3.1 g., m.p. 65°–145°C. Several recrystallizations from n-butyl chloride yields a material with m.p. 176°–178.5°C.

Anal. Calcd. for $C_{26}H_{22}Cl_2O_3$: C, 68.88; H, 4.89; Found: C, 68.70; H, 5.08.

EXAMPLE 10

4-(m-Chlorobenzyl)-4-phenyl-5-oxo-7-(p-chlorophenyl)-6-heptenoic Acid p-Chlorobenzaldehyde (3.5 g., 0.025 mole) in ethanol (10 ml.) is added to a solution of 4-(m-chlorobenzyl)-4-phenyl-5-oxohexanoic acid (4.89 g., 0.015 mole) and sodium hydroxide (0.8 g., 0.02 mole) in water (50 ml.). The resulting mixture is heated on a steam bath for 24 hours. The reaction solution is cooled to room temperature, diluted with water (200 ml.) and extracted with ether to remove the excess p-chlorobenzaldehyde. Ether is expelled from the aqueous phase by warming. The solution is cooled in an ice bath, acidified with dilute hydrochloric acid (10 ml.), and the white solid which precipitates is collected and air-dried to yield 5.05 g., m.p. 65°–130°C. Several recrystallizations from n-butyl chloride and petroleum ether (30°–60°C.) give a material with m.p. 137°–139°C.

Anal. Calcd. for $C_{26}H_{22}Cl_2O_3$: C, 68.88; H, 4.89; Found: C, 69.16; H, 4.90.

EXAMPLE 11

Levo-4-(o-chlorobenzyl)-4-phenyl-5-oxo-7-(2,6-dichlorophenyl)-6-heptenoic Acid 2,6-Dichlorobenzaldehyde (4.38 g., 0.025 mole) in ethanol (10 ml.) is added to a solution of levo-4-(o-chlorobenzyl)-4-phenyl-5-oxohexanoic acid (4.89 g., 0.015 mole) and sodium hydroxide (0.8 g., 0.02 mole) in water (50 ml.). The resulting mixture is heated on a steam bath for 24 hours. The reaction solution is cooled to room temperature, diluted with water (200 ml.) and extracted with ether to remove the excess 2,6-dichlorobenzaldehyde. Ether is expelled from the aqueous phase by warming. The solution is cooled to room temperature, acidified with dilute hydrochloric acid (10 ml.), and the gummy oil which separates is extracted into ether. The ether extract is washed with brine solution, and dried ($Na_2SO_4$). Removal of the ether in vacuo, yields a yellowish residue which after recrystallization from a mixture of n-butyl chloride and petroleum ether (30°–60°C.) gives a white material, 1.75 g., m.p. 140.5°–143°C.

Anal. Calcd. for $C_{26}H_{21}Cl_3O_3$: C, 64.01; H, 4.34; Found: C, 63.88; H, 4.37.

EXAMPLE 12

Levo-4-(o-chlorobenzyl)-4-phenyl-5-oxo-7-(p-chlorophenyl)-6-heptenoic Acid p-Chlorobenzaldehyde (10.5 g., 0.075 mole) in ethanol (30 ml.) is added to a solution of levo-4-(2-chlorobenzyl)-4-phenyl-5-oxohexanoic acid (14.67 g., 0.045 mole) and sodium hydroxide (2.40 g., 0.06 mole) in water (150 ml.). The resulting mixture is heated on a steam bath for 24 hours. The reaction solution is cooled to room temperature, acidified with dilute hydrochloric acid (30 ml.), and the solid (yellow) which forms after scratching is filtered and air-dried to yield 24.1 g. of material with m.p. 150°–165°C. (sinters at 140°). Several recrystallizations from n-butyl chloride, followed by several recrystallizations from acetonitrile gives a white solid, m.p. 189°–190°C., $[\alpha]_D^{25} = -61.5$ (in 1% $CHCl_3$).

Anal. Calcd. for $C_{26}H_{22}Cl_2O_3$: C, 68.88; H, 4.89; Found: C, 68.85; H, 4.82.

EXAMPLE 13

4-(o-Chlorocinnamyl)-4-phenyl-5-oxo-7-(p-chlorophenyl)-6-heptenoic Acid

Step A: 6-(o-Chlorophenyl)-3-phenyl-5-hexen-2-one Sodium hydride (6.30 g., 0.15 mole, oil dispersion) is suspended in glyme (200 ml.) and phenyl acetone (20.13 g., 0.15 mole) is added dropwise with stirring. After complete addition, the mixture is heated to reflux for one hour. The mixture is cooled to room temperature, and a solution of crude o-chlorocinnamyl bromide (39.05 g., 0.17 mole) in glyme (100 ml.) is added dropwise with stirring. When addition is complete, the mixture is heated on a steam bath for 24 hours then allowed to cool. Filtration and removal of solvent in vacuo produces a yellow oil. This oil is taken up in ether (400 ml.), washed with a very dilute hydrochloric acid solution, followed by a washing with brine, and is finally dried over $Na_2SO_4$. Filtration and removal of solvent in vacuo yields the crude product as a dark oil. Vacuum distillation provides 24.9 g., b.p. 153°–155°/0.1 mm.

Step B: 4-(o-Chlorocinnamyl)-4-phenyl-5-oxohexanitrile

Triton B (1.75 ml., 40% in $H_2O$) is added to a suspension of 6-(o-chlorophenyl)-3-phenyl-5-hexen-2-one (24.21 g., 0.085 mole) in t-butanol (100 ml.) followed by a slow dropwise addition of acrylonitrile (5.41 g., 0.102 mole). After three hours of stirring, the reaction mixture is acidified (dilute $H_2SO_4$) and allowed to stir an additional 0.5 hour at room temperature. The tan solid which forms is collected and air-dried to give 22.0 g. of material. Recrystallization from cyclohexane yields 21.1 g. of material with m.p. 125°–127.5°C.

Step C: 4-(o-Chlorocinnamyl)-4-phenyl-5-oxohexanoic Acid 4-(2-Chlorocinnamyl)-4-phenyl-5-oxohexanitrile (21.1 g., 0.062 mole) is added to a mixture of concentrated sulfuric acid (35 ml.), glacial acetic acid (150 ml.) and water (45 ml.), and the resulting mixture is heated to reflux. After refluxing for 1.5 hours, the cooled reaction mixture is slowly poured into cold water (1000 ml.). The aqueous solution is decanted off from a gummy residue that forms, and this residue is dissolved in ether. The ether extract is washed with brine solution, and dried over anhydrous $Na_2SO_4$. Filtration and removal of the ether in vacuo yields a yellow residue which upon trituration with hexane (200 ml.) produces 20.0 g. (air-dried) of an off-white solid, m.p. 95°–110°C. Recrystallization from cyclohexane gives a material with m.p. 117°–121.5°C.

Anal. Calcd. for $C_{21}H_{21}ClO_3$: C, 70.68; H, 5.93; Found: C, 70.97; H, 6.04.

Step D: 4-(o-Chlorocinnamyl)-4-phenyl-5-oxo-7-(p-chlorophenyl)-6-heptenoic Acid p-Chlorobenzaldehyde (2.81 g., 0.02 mole) in ethanol (10 ml.) is added to a solution of 4-(o-chlorocinnamyl)-4-phenyl-5-oxohexanoic acid (3.57 g., 0.01 mole) and sodium hydroxide (0.56 g., 0.014 mole) in water (50 ml.). The resulting mixture is heated on a steam bath for 24 hours. The reaction solution is cooled to room temperature, diluted with water (250 ml.), and extracted with ether to remove the excess p-chlorobenzaldehyde. The aqueous phase is acidified with dilute hydrochloric acid (10 ml.), and the gum that separates out is extracted into ether. The ether extract is washed with brine solution, and dried over anhydrous $Na_2SO_4$. Filtration and removal of the ether in vacuo gives a viscous yellow residue, which upon trituration with petroleum ether (30°–60°C., 150 ml.) yields 4.3 g. of material, m.p. 90°–125°C. (cloudy). Recrystallization from n-butyl chloride, followed by ethanol, produces a material with m.p. 143°–146°C.

Anal. Calcd. for $C_{28}H_{24}Cl_2O_3$: C, 70.15; H, 5.05; Found: C, 70.10; H, 5.40.

EXAMPLE 14

4-(o-Chlorocinnamyl)-4-phenyl-5-oxo-7-(o-methoxyphenyl)-6-heptenoic Acid o-Methoxybenzaldehyde (2.72 g., 0.02 mole) in ethanol (10 ml.) is added to a solution of 4-(o-chlorocinnamyl)-4-phenyl-5-oxohexanoic acid (3.57 g., 0.01 mole) and sodium hydroxide (0.56 g., 0.014 mole) in water (50 ml.). The resulting mixture is heated on a steam bath for 24 hours. The reaction solution is cooled to room temperature, diluted with water (200 ml.), and extracted with ether to remove the excess o-methyoxybenzaldehyde. Ether is expelled from the aqueous phase by warming. The solution is cooled in an ice bath, acidified with dilute hydrochloric acid (10 ml.), and the yellow solid which precipitates is collected and air-dried. Several recrystallizations from ethanol yields a pale yellow material with m.p. 206.5°–209.5°C.

Anal. Calcd. for $C_{29}H_{27}ClO_4$: C, 73.33; H, 5.73; Found: C, 72.96; H, 5.82.

EXAMPLE 15

4-(p-Chlorocinnamyl)-4-phenyl-5-oxo-7-(p-chlorophenyl)-6-heptenoic Acid

Step A: 6-(p-Chlorophenyl)-3-phenyl-5-hexen-2-one

Sodium hydride (9.79 g., 0.233 mole, oil dispersion) is suspended in glyme (500 ml.) and phenylacetone (31.26 g., 0.233 mole) is added dropwise with stirring. After complete addition, the mixture is heated to reflux for one hour. The mixture is cooled to room temperature and a solution of p-chlorocinnamyl bromide (53.85 g., 0.233 mole) in glyme (100 ml.) is added dropwise. When addition is complete, the mixture is refluxed for 24 hours then allowed to cool. After filtration of inorganic salts and removal of solvent from the filtrate, vacuum distillation provides 36.22 g., b.p. 158°–160°/0.1 mm.

Step B: 1,7-bis-(p-Chlorophenyl)-4-phenyl-1,6-heptadien-3-one

A sodium hydroxide solution (7.5 ml., 20%) is added to a solution of p-chlorobenzaldehyde (17.86 g., 0.127 mole) and 3-phenyl-6-(p-chlorophenyl)-5-2-one (36.22 g., 0.127 mole) in ethanol (360 ml.) with stirring. The off-white solid that separates on continued stirring is filtered and air-dried, 45.0 g., m.p. 115°–118°C. Recrystallization from ethanol gives material with m.p. 117°–119°C.

Step C: 4-(p-Chlorocinnamyl)-4-phenyl-5-oxo-7-(p-chlorophenyl)-6-heptenoic Acid

Triton B (1 ml., 40% in MeOH) is added to a stirred solution of 1,7-bis-(p-chlorophenyl)-4-phenyl-1,6-heptadien-3-one (16.10 g., 0.039 mole) in glyme (150 ml.), followed by addition of methyl acrylate (3.87 g., 0.045 mole) in glyme (25 ml.). After stirring for 24 hours, the solvent is removed in vacuo and water (600 ml.) and dilute hydrochloric acid (25 ml.) are added to the residue. The organic material is extracted into ether and these extracts are washed with water, saturated brine and dried ($Na_2SO_4$). After removal of the solvent, the residue is heated on a steam bath with a solution of 20% sodium hydroxide (20 ml.) in methanol (300 ml.) for 20 hours. The methanol is removed in vacuo and the residue is dissolved in water (1200 ml.). Extraction with ether removes unreacted ketone. Ether is expelled from the aqueous phase by warming. The solution is cooled in an ice bath, acidified with dilute hydrochloric acid (25 ml.) and the solid (yellowish) that precipitates is filtered and air-dried; yield 16.5 g., m.p. 75°–173°C. Several recrystallizations from n-butyl chloride gives material with m.p. 178.5°–180°C.

Anal. Calcd. for $C_{28}H_{24}Cl_2O_3$: C, 70.15; H, 5.05; Found: C, 69.77; H, 5.12.

EXAMPLE 16

4-(m-Chlorocinnamyl)-4-phenyl-5-oxo-2-(p-chlorophenyl)-6-heptenoic Acid

Step A: 6-(m-Chlorophenyl)-3-phenyl-5-hexen-2-one

Sodium hydride (25.20 g., 0.60 mole, oil dispersion) is suspended in glyme (800 ml.) and phenyl acetone (80.50 g., 0.60 mole) in glyme (100 ml.) is added dropwise with stirring. After complete addition the mixture is heated to reflux for one hour. The mixture is cooled to room temperature and a solution of crude m-chlorocinnamyl bromide (139 g., 0.6 mole) in glyme (100 ml.) is added dropwise. When addition is complete the mixture is refluxed for 24 hours then allowed to cool. After filtration of inorganic salts and removal of solvent from the filtrate, vacuum distillation provides 36.11 g., b.p. 158.5°–163°/0.1 mm.

Step B: 1-(p-Chlorophenyl)-7-(m-chlorophenyl)-4-phenyl-1,6-heptadien-3-one

A sodium hydroxide solution (7.5 ml., 20%) is added to a solution of p-chlorobenzaldehyde (17.86 g., 0.127 mole) and 3-phenyl-6-(m-chlorophenyl)-5-hexen-2-one (36.11 g., 0.127 mole) in ethanol (360 ml.) with stirring. The gum that separates on continued stirring is chromatographed (benzene) through a silica gel column to obtain the product as a very viscous oil (opaque).

Step C: 4-(m-Chlorocinnamyl)-4-phenyl-5-oxo-7-(p-chlorophenyl)-6-heptenoic Acid

Triton B (1.5 ml., 40% in MeOH) is added to a stirred solution of 1-(p-chlorophenyl)-4-phenyl-7-(m-chlorophenyl)-1,6-heptadien-3-one (22.8 g., 0.056 mole) in glyme (175 ml.), followed by addition of methyl acrylate (5.76 g., 0.067 mole) in glyme (25 ml.). After stirring for 20 hours, the solvent is removed in vacuo and water (600 ml.) and dilute hydrochloric acid (25 ml.) are added to the residue. The organic material is extracted into ether and these extracts are washed with water, saturated brine and dried ($Na_2SO_4$). After removal of the solvent the residue is heated on a steam bath with a solution of 20% sodium hydroxide (25 ml.) in methanol (300 ml.) for 48 hours. The methanol is removed in vacuo and the residue is dissolved in water (1200 ml.). Extraction with ether removes unreacted ketone. Ether is expelled from the aqueous phase by warming. The solution is cooled in an ice bath, acidified with dilute hydrochloric acid (30 ml.), and the sticky yellow solid which precipitates is collected and air-dried, yield 4.5 g., m.p. 65°–105°C. Recrystallization from benzene-petroleum ether (30°–60°C.) followed by several recrystallizations from n-butyl chloride gives material with m.p. 150°–151°C.

Anal. Calcd. for $C_{28}H_{24}Cl_2O_3$: C, 70.15; H, 5.05; Found: C, 69.88; H, 5.06.

EXAMPLE 17

4-(o-Methylcinnamyl)-4-phenyl-5-oxo-7-(p-chlorophenyl)-6-heptenoic Acid

Step A: 3-Phenyl-6-(o-methylphenyl)-5-hexen-2-one

Sodium hydride (11.76 g., 0.28 mole, oil dispersion) is suspended in glyme (400 ml.) and phenyl acetone (37.57 g., 0.28 mole) in glyme (50 ml.) is added dropwise with stirring. After complete addition, the mixture is heated to reflux for one hour. The mixture is cooled to room temperature and a solution of crude o-methylcinnamyl bromide (59.10 g., 0.28 mole) in glyme (50 ml.) is added dropwise. When addition is complete, the mixture is heated on a steam bath for 24 hours then allowed to cool. After filtration of inorganic salts and removal of solvent from filtrate, a dark viscous residue is obtained. Trituration of this residue with petroleum ether (30°–60°C., 100ml.) produces tan solid, yield 26.5 g., m.p. 72°–75°C.

Step B: 1-(p-Chlorophenyl)-4-phenyl-7-(o-methylphenyl)-1,6-heptadien-3-one

A sodium hydroxide solution (5.5 ml., 20%) is added to a solution of p-chlorobenzaldehyde (14.06 g., 0.1 mole) and 3-phenyl-6-(o-methylphenyl)-5-hexen-2-one (26.4 g., 0.1 mole) in ethanol (260 ml.) with stirring. The yellowish solid that separates on continued stirring is filtered and air-dried, yield 22.5 g., m.p. 60°–76°C. Recrystallization from hexane gives material with m.p. 79°–82°C.

Step C: 4-(o-Methylcinnamyl)-4-phenyl-5-oxo-7-(p-chlorophenyl)-6-heptenoic Acid

Triton B (1 ml., 40% in MeOH) is added to a stirred solution of 1-(p-chlorophenyl)-4-phenyl-7-(o-methylphenyl)-1,6-heptadien-3-one (15.47 g., 0.04 mole) in glyme (150 ml.), followed by addition of methyl acrylate (4.13 g., 0.048 mole) in glyme (25 ml.). After stirring for 24 hours, the solvent is removed in vacuo, and water (600 ml.) and dilute hydrochloric acid (25 ml.) are added to the residue. The organic material is extracted into ether and these extracts are washed with water, saturated brine and dried ($Na_2SO_4$). After removal of the solvent, the residue is heated on a steam bath with a solution of 20% sodium hydroxide (25 ml.) in methanol (300 ml.) for 20 hours. The methanol is removed in vacuo and the residue is dissolved in water (1200 ml.). Extraction with ether removes unreacted ketone. Ether is expelled from the aqueous phase by warming. The solution is cooled in an ice bath, acidified with dilute hydrochloric acid (30 ml.), and the yellowish solid that precipitates is filtered and air-dried; yield 12.85 g., m.p. 60°–80°C. (glass). Several recrystallizations from n-butyl chloride, followed by a final recrystallization and ethanol gives material with m.p. 163.5°–165°C. Anal. Calcd. for $C_{29}H_{27}ClO_3$: C, 75.89; H, 5.93; Found: C, 75.67; H, 5.76.

EXAMPLE 18

Metyl levo-4-(o-chlorobenzyl)-4-phenyl-5-oxo-7-(p-chlorophenyl)-6-heptenoate

Concentrated sulfuric acid (4.5 ml.) is slowly added to a mixture of levo-4-(o-chlorobenzyl)-4-phenyl-5-oxo-7-(p-chlorophenyl)-6-heptenoic acid (9.07 g., 0.02 mole) and methanol (200 ml.). This mixture is refluxed with stirring for four hours then cooled to room temperature. The solid (white) which crystallizes out is filtered, washed with some fresh methanol and airdried to give 8.8 g., of material with m.p. 116°–117.5°C. Recrystallization from hexane produces white needles, m.p. 116.5°–118°C.

Anal. Calcd. for $C_{27}H_{24}Cl_2O_3$: C, 69.38; H, 5.18; Found: C, 69.36; H, 5.27.

EXAMPLE 19

Pentyl levo-4-(o-chlorobenzyl)-4-phenyl-5-oxo-7-(p-chlorophenyl)-6-heptenoate

Concentrated sulfuric acid (4.5 ml.) is slowly added to a mixture of levo-4-(o-chlorobenzyl)-4-phenyl-5- oxo-7-(p-chlorophenyl)-6-heptenoic acid (9.07 g., 0.02 mole) and pentanol (200 ml.). This mixture is heated at 100°–120°C. by means of a heating mantel then cooled in an ice-water bath for one hour. The white solid which crystallizes is collected and air-dried to give 8.4 g. of material with m.p. 78°–81.5°C. Two recrystallizations from hexane yields a white crystalline solid, m.p. 82°–84°C.

Anal. Calcd. for $C_{31}H_{32}Cl_2O_3$: C, 71.12; H, 6.16; Found: C, 71.01; H, 6.22.

EXAMPLE 20

Decyl levo-4-(o-chlorobenzyl)-4-phenyl-5-oxo-7-(p-chlorophenyl)-6-heptenoate A mixture of levo-4-(o-chlorobenzyl)-4-phenyl-5-oxo-7-(p-chlorophenyl)-6-heptenoic acid (9.07 g., 0.02 mole), decanol (3.17 g., 0.02 mole), p-toluenesulfonic acid monohydrate (200 mg.), and benzene (200 ml.) is heated under a Dean-Stark trap for 24 hours. The resulting reaction solution is cooled to room temperature, washed with saturated sodium bicarbonate solution to remove any unreacted acid, then washed with water and finally with saturated brine before drying over $Na_2SO_4$. Removal of the benzene in vacuo, produces a viscous oil (yellowish) which when taken up in petroleum ether (30°–60°C., 50 ml.) and cooled in a freezer overnight yields (upon rapid filtration) a white solid, m.p. 49°–53°C. This "petroleum ether-freezer" procedure, when repeated several times, gives essentially no change in melting point.

Anal. Calcd. for $C_{36}H_{42}Cl_2O_3$: C, 72.84; H, 7.13; Found: C, 73.20; H, 7.26.

EXAMPLE 21

Preparation of (levo)-4-(o-Chlorobenzyl)-4-phenyl-5-oxo-7-(3,4-dichlorophenyl)-6-heptenoic Acid A solution of (levo)-4-(o-chlorobenzyl)-4-phenyl-5-oxohexanoic acid (49.7 g.; 0.15 mole) and sodium hydroxide (8 g.; 0.2 mole) in water (250 ml.) is treated with a solution of 3,4-dichlorobenzaldehyde (35.00 g.; 0.2 mole) in 95% ethanol (75 ml.) and the mixture is heated under reflux for 10 hours.

The cooled reaction solution is acidified with 6N hydrochloric acid. An oil separates which slowly solidifies. The yield is 72.2 g. (100%), m.p. 120°–155°C. Recrystallization from acetonitrile gives 60.8 g. of solid, m.p. 166°–169°C. A second recrystallization from acetonitrile gives material melting at 173.5°–174.5°C.

Anal. Calcd. for $C_{26}H_{21}Cl_3O_3$: C, 64.01; H, 4.34; Cl, 21.81; Found: C, 64.16; H, 4.52; Cl, 21.73.

EXAMPLE 22

7-(p-Chlorophenyl)-4-cinnamyl-5-oxo-4-phenyl-6-heptenoic Acid

Step A: 3,6-Diphenyl-5-hexen-2-one

Sodium hydride (10.5 g., 0.25 mole, oil dispersion) is suspended in glyme (200 ml.) and phenyl acetone (33.5 g., 0.25 mole) in glyme (25 ml.) is added dropwise with stirring. After complete addition, the mixture is heated to reflux for 0.5 hours. The mixture is cooled in a cold water bath and a solution of cinnamyl chloride (38 g., 0.25 mole) in glyme (25 ml.) is added dropwise. When addition is complete, the mixture is refluxed for 5 hours then allowed to cool. After filtration of inorganic salts and removal of solvent from the filtrate, vacuum distillation provides 44 g., b.p. 128°–134°/0.07–0.1 mm.

Step B: 1-(p-Chlorophenyl)-4,7-diphenyl-1,6-heptadien-3-one

A sodium hydroxide solution (2.5 ml., 20%) is added to a solution of p-chlorobenzaldehyde (7.0 g., 0.05 mole) and 3,6-diphenyl-5-hexen-2-one (12.5 g., 0.05 mole) in ethanol (125 ml.) with stirring. The yellowish solid that separates on continued stirring is filtered, washed with cold ethanol, and air-dried, 14.35 g., m.p. 92°–95°C. Recrystallization from hexane gives material with m.p. 95°–96.5°C.

Step C: 4-Cinnamyl-4-phenyl-5-oxo-7-(p-chlorophenyl)-6-heptenoic Acid

Triton B (0.2 ml., 40% in MeOH) is added to a stirred solution of 1-(p-chlorophenyl)4,7-diphenyl-1,6-heptadien-3-one (3.72 g., 0.01 mole) in glyme (25 ml.), followed by addition of ethyl acrylate (1.11 g., >0.01 mole). After stirring for 24 hours, glacial acetic acid (0.5 ml.) is added and the solvent removed under reduced pressure. The residue is mixed with a solution of sodium hydroxide (0.80 g., 0.02 mole) in water (15 ml.) and methanol (150 ml.) and stirred for 24 hours. The methanol is removed in vacuo and the residue is dissolved in water (200 ml.). Extraction with ether removes unreacted ketone. Ether is expelled from the aqueous phase and it is acidified to Congo Red with dilute hydrochloric acid. The off-white solid that separates is collected, washed well with water, and air-dried, yield 3 g. Recrystallization from benzene-hexane gives material with m.p. 135°–140°C.

Anal. Calcd. for $C_{28}H_{25}ClO_3$: C, 75.58; H, 5.66; Found: C, 75.71; H, 5.64.

EXAMPLE 23

4-(p-Methylcinnamyl)-4-phenyl-5-oxo-7-(p-chlorophenyl-6-heptenoic Acid

Step A: 3-Phenyl-6-(p-methylphenyl)-5-hexen-2-one

Sodium hydride (6 g., 0.14 mole, oil dispersion) is suspended in glyme (200 ml.) and phenyl acetone (19.2 g., 0.14 mole) in glyme (50 ml.) is added dropwise with stirring. After complete addition the mixture is heated to reflux for 0.5 hour. The mixture is cooled in a cold water bath and a solution of p-methylcinnamyl bromide (32.2 g., 0.14 mole) in glyme (50 ml.) is added dropwise. When addition is complete, the mixture is refluxed for 18 hours then allowed to cool. Cold water (1000 ml.) is added and the mixture acidified with dilute hydrochloric acid. The mixture is saturated with ammonium sulfate and the organic material is extracted into ether. The extracts are washed with water, saturated brine, and dried (MgSO₄). Filtration and removal of solvent in vacuo produces the crude product as a dark oil.

Step B: 1-(p-Chlorophenyl)-4-phenyl-7-(p-methylphenyl)-1,6-heptadien-3-one

A sodium hydroxide solution (8 ml., 20%) is added to a solution of p-chlorobenzaldehyde (20.4 g., 0.14 mole) and crude 3-phenyl-6-(p-methylphenyl)-5-hexen-2-one (Step A, above) in ethanol (350 ml.) with stirring. The off-white solid that separates on continued stirring is filtered, washed with cold ethanol and air-dried, yield 44 g., m.p. 114°–118°C. Recrystallization from ethanol gives material with m.p. 134°–136.5°C.

15

Step C: 4-(p-Methylcinnamyl)-4-phenyl-5-oxo-7-(p-chlorophenyl)-6-heptenoic Acid

Triton B (1 ml., 40% in MeOH) is added to a stirred suspension of 1-(p-chlorophenyl)-4-phenyl-7-(p-methylphenyl)-1,6-heptadien-3-one (14.55 g., 0.038 mole) in glyme (150 ml.) followed by addition of methyl acrylate (3.87 g., 0.045 mole) in glyme (25 ml.). The mixture is warmed slightly to obtain solution then is stirred for 24 to 48 hours. The solvent is removed under reduced pressure and water (1000 ml.) and dilute hydrochloric acid is added to the residue. The organic material is extracted into ether and these extracts are washed with water, saturated brine and dried ($MgSO_4$). After removal of the solvent the residue is heated with a solution of 20% sodium hydroxide (20 ml.) in methanol (800 ml.) on the steam bath for 24 hours. The methanol is removed in vacuo and the residue is dissolved in a large volume of water. Extraction with ether removes unreacted ketone. Ether is expelled from the aqueous phase by warming and dilute hydrochloric acid is added. The solid that separates is collected, washed well with water, and air-dried, yield 10.43 g., m.p. 170°–180°C. Recrystallization from acetonitrile gives material with m.p. 182°–185°C.

Anal. Calcd. for $C_{29}H_{27}ClO_3$: C, 75.89; H, 5.93; Found: C, 76.11; H, 5.92.

EXAMPLE 24

4-(m-Methylcinnamyl)-7-(p-chlorophenyl)-5-oxo-4-phenyl-6-heptenoic Acid

Step A: 3-Phenyl-6-(m-methylphenyl)-5-hexen-2-one

Sodium hydride (6 g., 0.14 mole, oil dispersion) is suspended in glyme (250 ml.) and phenyl acetone (18.6 g., 0.14 mole) in glyme (50 ml.) is added dropwise with stirring. After complete addition the mixture is heated to reflux for one hour. The mixture is cooled in a cold water bath and a solution of m-methylcinnamyl bromide (29.16 g., 0.14 mole) in glyme (50 ml.) is added dropwise. When addition is complete the mixture is refluxed for 20 hours. The cooled mixture is filtered and the filtrate is evaporated under reduced pressure. The residue is dissolved in ether and washed with dilute hydrochloric acid, water and saturated brine. After drying ($MgSO_4$) and evaporation of ether the residue is vacuum distilled and the product is collected at 161°–164°/0.4 mm; 25.24 g.

Step B: 1-(p-Chlorophenyl)-4-phenyl-7-(m-methylphenyl)-1,6-heptadien-3-one

A 20% sodium hydroxide solution (5 ml.) is added to a stirred solution of p-chlorobenzaldehyde (14 g., 0.1 mole) and 3-phenyl-6-(m-methylphenyl)-5-hexen-2-one (25.24 g., 0.096 mole) in ethanol (250 ml.). The yellowish solid that separates on continued stirring is collected, washed with cold ethanol, and air-dried, yield 34.9 g., m.p. 89°–93°C. Recrystallization from ethanaol produces material with m.p. 95°–98°C.

Step C: 4-(m-Methylcinnamyl)-4-phenyl-5-oxo-7-(p-chlorophenyl)-6-heptenoic Acid

Triton B (2 ml., 40% in MeOH) is added to a stirred solution of 1-(p-chlorophenyl)-4-phenyl-7-(m-methylphenyl)-1,6-heptadien-3-one (19.33 g., 0.05 mole) in glyme (250 ml.) followed by the addition of methyl acrylate (4.73 g., 0.055 mole) in glyme (50 ml.). The solution is stirred for 96 hours and the solvent is removed under reduced pressure. The residue is suspended in methanol (700 ml.) and a 20% sodium hydroxide solution (35 ml.) is added. After an additional 24 hours, the methanol is evaporated in vacuo and the

16 residue is dissolved in water. Extraction with ether removes unreacted ketone. The aqueous solution is acidified and the solid that separates is collected, washed well with water, and air-dried, yield 9.78 g., m.p. 135°–144°C. Recyrstallization from butyl chloride produces material with m.p. 154°–155°C.

Anal. Calcd. for $C_{29}H_{27}ClO_3$: C, 75.89; H, 5.93; Found: C, 76.08; H, 5.94.

EXAMPLE 25

4-Benzyl-4-phenyl-5-oxo-7-(p-chlorophenyl)-6-heptenoic Acid

Step A: 3,4-Diphenyl-2-butanone

Sodium hydride (8.4 g., 0.2 mole, oil dispersion) is suspended in glyme (400 ml.) and phenyl acetone (26.8 g., 0.2 mole) in glyme (50 ml.) is added dropwise with stirring. After complete addition the mixture is heated to reflux for one hour then cooled in a cold water bath. A solution of benzyl chloride (25.3 g., 0.2 mole) in glyme (50 ml.) is added then the mixture is refluxed for 12 hours. Removal of the inorganic salts by filtration followed by vacuum distillation of the residue gives 31.06 g., b.p 104°–107°/0.1 mm Step B: 1-(p-Chlorophenyl)-4,5-diphenyl-1-penten-3-one A 20% sodium hydroxide solution (10 ml.) is added to a stirred solution of p-chlorobenzaldehyde (19.4 g., 0.138 mole) and 3,4-diphenyl-2-butanone (31.06 g., 0.138 mole) in ethanol (400 ml.). The cream-colored solid that separates is collected, washed with water, and dried at 90°C., yield 41.13 g., m.p. 113°–115°C. Recrystallization from ethanol gives material with m.p. 117°–118.5 C.

Step C: 4-Benzyl-4-phenyl-5-oxo-7-(p-chlorophenyl)-6-heptenoic Acid

Triton B (2 ml., 40% in MeOH) is added to a stirred solution of 1-(p-chlorophenyl)-4,5-diphenyl-1-penten-3-one (17.33 g., 0.05 mole) in glyme (200 ml.) followed by addition of methyl acrylate (4.73 g., 0.055 mole) in glyme (50 ml.). The solution is stirred for 96 hours and the solvent is removed under reduces pressure. The residue is dissolved in methanol (500 ml.) and a 20% sodium hydroxide solution (25 ml.) is added. After an additional 24 hours, the methanol is evaporated in vacuo and the residue is dissolved in water. Extraction with ether removes unreacted ketone. Acidification produces 16.18 g., m.p. 160°–170°C. when collected and air-dried. Recrystallization from butyl chloride gives material with m.p. 173°–176°C.

Anal. Calcd. for $C_{26}H_{23}ClO_3$: C, 74.55; H, 5.53; Found: C, 74.81; H, 5.52.

What is claimed is:
1. The compound having the formula

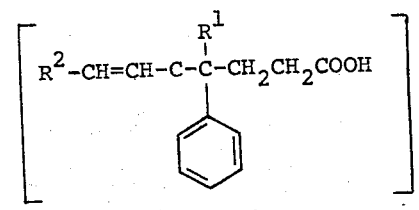

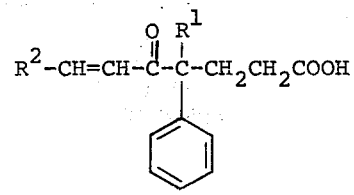

wherein $R^1$ is benzyl or cinnamyl, which may be substituted with 1 or 2 substituents selected from halo, dihalo, loweralkyl, diloweralkyl, loweralkoxy, or dilower-alkoxy; and $R^2$ is phenyl, or phenyl substituted with 1 or 2 substituents, selected from lower-alkyl, diloweralkyl, loweralkoxy, or diloweralkoxy.

2. The compound of claim 1 wherein $R^1$ is o-chlorobenzyl and $R^2$ is p-chlorophenyl.

3. The compound of claim 1 wherein $R^1$ is cinnamyl and $R^2$ is p-chlorophenyl.

4. The compound of claim 1 wherein $R^1$ is o-chlorobenzyl and $R^2$ is p-methyloxyphenyl.

5. The compound of claim 1 wherein $R^1$ is p-chlorocinnamyl and $R^2$ is p-chlorophenyl.

6. The compound of claim 1 wherein $R^1$ is p-methylcinnamyl and $R^2$ is p-chlorophenyl.

7. The compound of claim 1 wherein $R^1$ is o-chlorobenzyl and $R^2$ is 3,4-dichlorophenyl.

8. The compound of claim 1 wherein $R^1$ is o-methylcinnamyl and $R^2$ is p-chlorophenyl.

* * * * *

UNITED STATES PATENT OFFICE
CERTIFICATE OF CORRECTION

PATENT NO. : 3,956,374
DATED : May 11, 1976
INVENTOR(S) : Kenneth L. Shepard et al.

It is certified that error appears in the above–identified patent and that said Letters Patent are hereby corrected as shown below:

Column 16, Line 60, delete the following:

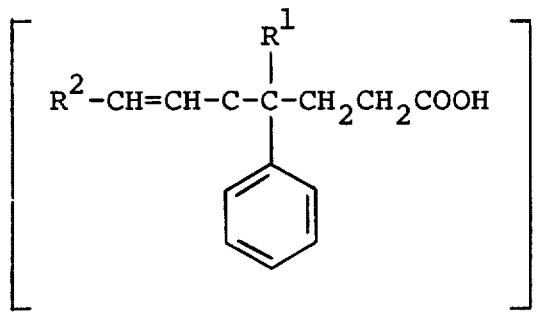

Signed and Sealed this

Seventh Day of December 1976

[SEAL]

Attest:

RUTH C. MASON
*Attesting Officer*

C. MARSHALL DANN
*Commissioner of Patents and Trademarks*